(12) United States Patent
Nakashima et al.

(10) Patent No.: US 10,414,908 B2
(45) Date of Patent: Sep. 17, 2019

(54) COMPOSITION FOR DIP MOLDING AND DIP-MOLDED ARTICLE

(71) Applicant: ZEON CORPORATION, Tokyo (JP)

(72) Inventors: Tomonori Nakashima, Tokyo (JP); Hiroyasu Nagamori, Tokyo (JP); Sayaka Inoue, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 288 days.

(21) Appl. No.: 15/128,163

(22) PCT Filed: Mar. 24, 2015

(86) PCT No.: PCT/JP2015/058978
§ 371 (c)(1),
(2) Date: Sep. 22, 2016

(87) PCT Pub. No.: WO2015/147010
PCT Pub. Date: Oct. 1, 2015

(65) Prior Publication Data
US 2017/0088700 A1 Mar. 30, 2017

(30) Foreign Application Priority Data
Mar. 28, 2014 (JP) ................................ 2014-068761

(51) Int. Cl.
| | | |
|---|---|---|
| *C08L 15/00* | (2006.01) | |
| *B29C 41/14* | (2006.01) | |
| *C08C 19/02* | (2006.01) | |
| *C08J 5/02* | (2006.01) | |
| *A61B 42/10* | (2016.01) | |
| *A41D 19/00* | (2006.01) | |
| *B29C 41/00* | (2006.01) | |
| *C08L 9/04* | (2006.01) | |
| *C08L 13/02* | (2006.01) | |
| *B29K 19/00* | (2006.01) | |
| *B29K 105/00* | (2006.01) | |
| *B29L 31/48* | (2006.01) | |

(52) U.S. Cl.
CPC ........ *C08L 15/005* (2013.01); *A41D 19/0082* (2013.01); *A61B 42/10* (2016.02); *B29C 41/003* (2013.01); *B29C 41/14* (2013.01); *C08C 19/02* (2013.01); *C08J 5/02* (2013.01); *C08L 9/04* (2013.01); *C08L 13/02* (2013.01); *C08L 15/00* (2013.01); *B29K 2019/00* (2013.01); *B29K 2105/0064* (2013.01); *B29L 2031/4864* (2013.01); *C08J 2309/04* (2013.01)

(58) Field of Classification Search
CPC ........... C08L 9/04; C08L 15/005; C08C 19/02
USPC ............................................. 524/821; 2/168
See application file for complete search history.

(56) References Cited

U.S. PATENT DOCUMENTS

| | | | | |
|---|---|---|---|---|
| 5,014,362 | A | * | 5/1991 | Tillotson ............ A41D 19/0055 2/167 |
| 6,844,385 | B1 | | 1/2005 | Hagiwara et al. |
| 8,153,712 | B2 | * | 4/2012 | Nagamori .............. C08K 5/005 524/186 |
| 2005/0154122 | A1 | | 7/2005 | Ota et al. |
| 2006/0235158 | A1 | | 10/2006 | Ota et al. |
| 2006/0253956 | A1 | | 11/2006 | Lipinski |
| 2006/0257674 | A1 | | 11/2006 | Lipinski et al. |
| 2008/0207809 | A1 | | 8/2008 | Koide |
| 2008/0227913 | A1 | | 9/2008 | Koide |
| 2008/0255314 | A1 | | 10/2008 | Ota et al. |
| 2009/0105424 | A1 | * | 4/2009 | Kodama ................. B29C 41/14 525/331.9 |
| 2011/0229646 | A1 | * | 9/2011 | Kim ...................... C08F 236/12 427/385.5 |
| 2011/0287254 | A1 | | 11/2011 | Lipinski |
| 2012/0137404 | A1 | | 6/2012 | Lipinski |
| 2012/0291180 | A1 | | 11/2012 | Lipinski |
| 2013/0198933 | A1 | | 8/2013 | Khoo et al. |
| 2013/0276208 | A1 | | 10/2013 | Lipnski |
| 2014/0206250 | A1 | | 7/2014 | Nakashima et al. |
| 2014/0302265 | A1 | | 10/2014 | Yang et al. |
| 2016/0053095 | A1 | | 2/2016 | Lipinski |

FOREIGN PATENT DOCUMENTS

| | | |
|---|---|---|
| CN | 1646587 A | 7/2005 |
| CN | 1829751 A | 9/2006 |
| EP | 1 143 817 A1 | 10/2001 |
| EP | 1 234 851 A1 | 8/2002 |
| EP | 1 964 882 A1 | 9/2008 |
| EP | 2 343 338 A1 | 7/2011 |
| JP | 2001-011126 A | 1/2001 |
| JP | 2004-002756 A | 1/2004 |
| JP | 2004-002768 A | 1/2004 |
| JP | 2007-177091 A | 7/2007 |
| JP | 2009-197149 A | 9/2009 |
| JP | 2009-235178 A | 10/2009 |
| JP | 2010-059441 A | 3/2010 |
| JP | 2012-057164 A | 3/2012 |
| JP | 2012-201856 A | 10/2012 |
| JP | 2013-213215 A | 10/2013 |
| KR | 2013-0056505 A | 5/2013 |
| WO | 00/47070 A1 | 8/2000 |
| WO | 2010/050552 A1 | 5/2010 |
| WO | 2013/031801 A1 | 3/2013 |

OTHER PUBLICATIONS

Mar. 14, 2017 extended Search Report issued in European Patent Application No. 15770234.1.

(Continued)

*Primary Examiner* — Fred M Teskin
(74) *Attorney, Agent, or Firm* — Oliff PLC

(57) ABSTRACT

A dip-molding composition of the present invention contains a latex (A) of a nitrile-group-containing highly saturated copolymer rubber (a). The nitrile-group-containing highly saturated copolymer rubber (a) contains an $\alpha,\beta$-ethylenically unsaturated nitrile monomer unit and a conjugated diene monomer unit, and being obtained by hydrogenating at least part of the conjugated diene monomer unit. A dip-molded article of the present invention is produced by dip molding of the above dip-molding composition.

6 Claims, No Drawings

(56) References Cited

OTHER PUBLICATIONS

Oct. 4, 2016 International Preliminary Report on Patentability issued in International Patent Application No. PCT/JP2015/058978.
Jun. 30, 2015 International Search Report issued in International Patent Application No. PCT/JP2015/058978.
Jul. 11, 2018 Office Action in European Patent Application No. 5770234.1.
Feb. 27, 2019 Office Action issued in European Application No. 15 770 234.1.

* cited by examiner

COMPOSITION FOR DIP MOLDING AND DIP-MOLDED ARTICLE

TECHNICAL FIELD

The present invention relates to (i) a composition for dip molding and (i) a dip-molded article.

BACKGROUND ART

Rubber gloves have been widely used for various purposes, for example, in housework, industries such as a food industry and an electronic parts manufacturing industry, and medical cares (particularly, in surgeries).

Rubber gloves in frequent use were conventionally gloves obtained by dip molding of natural rubber latex. Some users, however, may suffer allergic reactions to such a natural rubber latex glove, due to a trace amount of protein present in a rubber component. In light of this, synthetic rubber latex gloves free from the above concern of allergy are currently in general use. An example of such synthetic rubber latex gloves is a glove made from acrylonitrile-butadiene copolymer latex.

Patent Literature 1 discloses acid-modified nitrile rubber latex for dip molding. This acid-modified nitrile rubber, when dried, forms a film containing 50 wt % to 90 wt % of an insoluble content of methyl ethyl ketone, which insoluble content has a methyl-ethyl-ketone swelling degree of 3 to 15.

Patent Literature 2 discloses latex of a hydrogenated conjugated diene polymer that contains 100 ppm or less of a platinum group element originated from a hydrogenation catalyst.

Patent Literature 3 discloses a method of producing latex for dip molding. This method includes the step of copolymerizing a conjugated diene monomer, an ethylenically unsaturated nitrile monomer, another ethylenically unsaturated monomer, and the like.

CITATION LIST

Patent Literature

[Patent Literature 1]
Japanese Patent Application Publication Tokukai No. 2007-177091 (Publication date: Jul. 12, 2007)
[Patent Literature 2]
Japanese Patent Application Publication Tokukai No. 2004-2756 (Publication date: Jan. 8, 2004)
[Patent Literature 3]
Japanese Patent Application Publication Tokukai No. 2012-201856 (Publication date: Oct. 22, 2012)

SUMMARY OF INVENTION

Technical Problem

Although gloves made from acrylonitrile-butadiene copolymer latex are free from concerns arising from a trace amount of protein contained in natural rubber latex, such gloves have problems of poor tensile strength that may cause a tear of a glove during use, and poor tolerance to an environment where a variation range of temperature is large.

As disclosed in Patent Literature 1, during production of a dip-molded article, the dip-molded article may undergo heat treatment at a temperature of 100° C. to 150° C. for sufficiently removing water from the molded article. For this reason, desirably, dip-molded articles are less likely to be affected by thermal history.

Meanwhile, in a case where dip-molded articles are transported by ship, the ship may travel through, for example, hot regions near the equator. In such a case, the temperature in a hold of the ship becomes extremely high. Thereafter, when the dip-molded articles have been delivered to a destination and sold as commercial products, some dip-molded articles may be used in a cold environment. In light of the above, the dip-molded articles need to have cold resistance even after heat aging so that the dip-molded articles can be satisfactorily used regardless of thermal history including a wide variation range of temperature to which the dip-molded articles have been exposed.

An object of the present invention is to provide (i) a dip-molding composition which makes it possible to provide a new dip-molded article having excellent tensile strength and excellent post-heat-aging cold resistance, and (ii) a dip-molded article produced by dip molding of the dip-molding composition.

Solution to Problem

It is not possible to tell whether or not a certain type of latex has an intended performance when dip-molded, before a dip-molding composition containing the latex is actually dip-molded. Further, it is not possible to tell whether or not a certain type of latex can be used for dip molding unless the latex is known to have excellent compatibility with a crosslinking agent and/or the like. Accordingly, unless the latex is known to have excellent compatibility with a crosslinking agent and/or the like, it is difficult to arrive at using the latex for dip molding. The inventors of the present invention found that: (i) among numerous types of latex, latex (A) of a nitrile-group-containing highly saturated copolymer rubber (a) has excellent compatibility with a crosslinking agent and/or the like, which rubber (a) contains an $\alpha,\beta$-ethylenically unsaturated nitrile monomer unit and a conjugated diene monomer unit and is obtained by hydrogenating at least part of the conjugated diene monomer unit; and (ii) it is possible to obtain a dip-molded article having excellent tensile strength and excellent post-heat-aging cold resistance by dip molding of the dip-molding composition containing the latex (A).

That is, a dip-molding composition of the present invention contains a latex (A) of a nitrile-group-containing highly saturated copolymer rubber (a), the nitrile-group-containing highly saturated copolymer rubber (a) containing an $\alpha,\beta$-ethylenically unsaturated nitrile monomer unit and a conjugated diene monomer unit, and being obtained by hydrogenating at least part of the conjugated diene monomer unit.

Further, a dip-molded article of the present invention is produced by dip molding of the dip-molding composition.

Advantageous Effects of Invention

The present invention advantageously makes it possible to provide a new dip-molded article having excellent tensile strength and excellent post-heat-aging cold resistance.

DESCRIPTION OF EMBODIMENTS

<Dip-Molding Composition>

A dip-molding composition of the present invention contains a latex (A) of a nitrile-group-containing highly saturated copolymer rubber (a), the nitrile-group-containing highly saturated copolymer rubber (a) containing an α,β-ethylenically unsaturated nitrile monomer unit and a conjugated diene monomer unit, and being obtained by hydrogenating at least part of the conjugated diene monomer unit.

The latex (A) is typically latex in which particles of the nitrile-group-containing highly saturated copolymer rubber (a) are dispersed in an aqueous solvent, the nitrile-group-containing highly saturated copolymer rubber (a) containing an α,β-ethylenically unsaturated nitrile monomer unit and a conjugated diene monomer unit and being obtained by hydrogenating at least part of the conjugated diene monomer unit.

The aqueous solvent is typically water, but can be any mixture of water-soluble organic solvents such as methanol, ethanol, and acetone, as long as such an aqueous solvent does not impair dispersion stability of the particles of the nitrile-group-containing highly saturated copolymer rubber (a).

The particles of the nitrile-group-containing highly saturated copolymer rubber (a) typically have a number average particle diameter of 50 nm to 200 nm. The number average particle diameter can be measured with use of a dynamic-light-scattering particle size distribution analyzer.

<Nitrile-Group-Containing Highly Saturated Copolymer Rubber (a)>

The nitrile-group-containing highly saturated copolymer rubber (a) of the latex (A) contains an α,β-ethylenically unsaturated nitrile monomer unit and a conjugated diene monomer unit, and is obtained by hydrogenating at least part of the conjugated diene monomer unit.

[α,β-Ethylenically Unsaturated Nitrile Monomer]

An α,β-ethylenically unsaturated nitrile monomer of the α,β-ethylenically unsaturated nitrile monomer unit is not limited to a particular nitrile monomer. Examples of the α,β-ethylenically unsaturated nitrile monomer include acrylonitrile, methacrylonitrile, fumaronitrile, chloroacrylonitrile, and α-cyanoethyl acrylonitrile. Among the above examples, acrylonitrile and methacrylonitrile are more preferable, and acrylonitrile is still more preferable. These α,β-ethylenically unsaturated nitrile monomers can be used alone or in combination of two or more kinds.

A content of the α,β-ethylenically unsaturated nitrile monomer unit contained in the nitrile-group-containing highly saturated copolymer rubber (a) is not limited to a particular content, and is preferably 10 wt % to 50 wt %, more preferably 15 wt % to 45 wt %, and still more preferably 20 wt % to 40 wt %. The content of the α,β-ethylenically unsaturated nitrile monomer unit of 10 wt % or more makes it possible to obtain a dip-molded article having more excellent tensile strength. The content of the α,β-ethylenically unsaturated nitrile monomer unit of 50 wt % or less makes it possible to obtain a dip-molded article having excellent texture.

[Conjugated Diene Monomer]

A conjugated diene monomer of the conjugated diene monomer unit is not limited to a particular diene monomer. Examples of the conjugated diene monomer include 1,3-butadiene, isoprene, 2,3-dimethyl-1,3-butadiene, 2-ethyl-1,3-butadiene, 1,3-pentadiene, and chloroprene. Among the above examples, 1,3-butadiene and isoprene are more preferable, and 1,3-butadiene is still more preferable. These conjugated diene monomers can be used alone or in combination of two or more kinds.

A content of the conjugated diene monomer unit is not limited to a particular content, and is preferably 49.5 wt % to 89.5 wt %, more preferably 55 wt % to 84 wt %, and still more preferably 58 wt % to 76 wt %. The content of the conjugated diene monomer unit of 49.5 wt % or more makes it possible to obtain a dip-molded article having excellent texture. The content of the conjugated diene monomer unit of 89.5 wt % or less makes it possible to obtain a dip-molded article having more excellent tensile strength.

Note that at least part of the conjugated diene monomer unit contained in the nitrile-group-containing highly saturated copolymer rubber (a) is hydrogenated. This allows a resultant dip-molded article to have improved tensile strength and excellent post-heat-aging cold resistance. The conjugated diene monomer unit only needs to be partially hydrogenated. Meanwhile, the nitrile-group-containing highly saturated copolymer rubber (a) has an iodine value of more preferably 100 or less, and still more preferably 50 or less. If the conjugated diene monomer unit is at least partially hydrogenated such that the iodine value will be 100 or less, it will be possible to obtain a dip-molded article having more excellent tensile strength.

[α,β-Ethylenically Unsaturated Acid Monomer]

The nitrile-group-containing highly saturated copolymer rubber (a) preferably contains an αβ-ethylenically unsaturated acid monomer unit in addition to the α,β-ethylenically unsaturated nitrile monomer unit and the conjugated diene monomer unit (including a structural unit in which a carbon-carbon double bond of a conjugated diene monomer unit is hydrogenated). When the nitrile-group-containing highly saturated copolymer rubber (a) additionally contains the α,β-ethylenically unsaturated acid monomer unit, it is possible to obtain a dip-molded article having more excellent tensile strength.

In the nitrile-group-containing highly saturated copolymer rubber (a), an α,β-ethylenically unsaturated acid monomer of the α,β-ethylenically unsaturated acid monomer unit is not limited to a particular acid monomer. Examples of the α,β-ethylenically unsaturated acid monomer include an α,β-ethylenic ally unsaturated monomer that contains an acidic group such as a carboxyl group, a sulfonic acid group, and an acid anhydride group.

Specific examples of the α,β-ethylenically unsaturated monomer that contains a carboxyl group include: α,β-ethylenically unsaturated monocarboxylic acid monomers such as acrylic acid, methacrylic acid, ethacrylic acid, crotonic acid, and cinnamic acid; α,β-ethylenically unsaturated polycarboxylic acid monomers such as itaconic acid, maleic acid, fumaric acid, citraconic acid, and chloromaleic acid; and α,β-ethylenically unsaturated polycarboxylic acid partial ester monomers such as monomethyl fumarate, monoethyl fumarate, monobutyl fumarate, monomethyl maleate, monoethyl maleate, monobutyl maleate, mono-2-hydroxypropyl maleate, monomethyl itaconate, monoethyl itaconate, and monobutyl itaconate.

Specific examples of the α,β-ethylenically unsaturated monomer containing a sulfonic acid group include styrene-sulfonic acid.

Specific examples of the α,β-ethylenically unsaturated monomer containing an acid anhydride group include α,β-ethylenically unsaturated polycarboxylic acid anhydrides such as maleic acid anhydride, itaconic acid anhydride, citraconic acid anhydride.

These α,β-ethylenically unsaturated acid monomers can be used alone or in combination of two or more kinds.

Among the above α,β-ethylenically unsaturated acid monomers, an α,β-ethylenically unsaturated carboxylic acid monomer is preferable, an ethylenically unsaturated monocarboxylic acid monomer is more preferable, and methacrylic acid is particularly preferable.

Alternatively, the α,β-ethylenically unsaturated acid monomer can be an alkali metal salt or an ammonium salt.

In the nitrile-group-containing highly saturated copolymer rubber (a), a content of the α,β-ethylenically unsaturated acid monomer unit is not limited to a particular content, and is preferably 0.5 wt % to 10 wt %, more preferably 1 wt % to 8 wt %, and particularly preferably 2 wt % to 6 wt %. The content of the α,β-ethylenically unsaturated acid monomer unit of 0.5 wt % or more makes it possible to obtain a dip-molded article having more excellent tensile strength. Meanwhile, the content of the α,β-ethylenically unsaturated acid monomer unit of 10 wt % or less makes it possible to obtain a dip-molded article having excellent texture and more excellent fitting durability.

[Other Monomers]

The nitrile-group-containing highly saturated copolymer rubber (a) can contain, in addition to the α,β-ethylenically unsaturated nitrile monomer unit, the conjugated diene monomer unit (including a structural unit in which a carbon-carbon double bond of the conjugated diene monomer unit is hydrogenated), and the α,β-ethylenically unsaturated acid monomer unit, a unit(s) of another monomer(s) (which hereinafter may be referred to simply as "other monomer") that can be copolymerized with the α,β-ethylenically unsaturated nitrile monomer, the conjugated diene monomer, and the α,β-ethylenically unsaturated acid monomer.

The unit of the other monomer is not limited to a particular monomer unit. Examples of the unit of the other monomer include a unit of a vinyl aromatic monomer, a unit of an α,β-ethylenically unsaturated carboxylic acid ester monomer, a unit of an α,β-ethylenically unsaturated amide monomer, and a unit of an alkyl vinyl ether monomer.

Specific examples of the vinyl aromatic monomer include styrene, alkylstyrene, and vinylnaphthalene.

The α,β-ethylenically unsaturated carboxylic acid ester monomer can be an α,β-ethylenically unsaturated monocarboxylic acid ester monomer or an α,β-ethylenically unsaturated polycarboxylic acid ester monomer.

Specific examples of the α,β-ethylenically unsaturated monocarboxylic acid ester monomer include an acrylic acid ester monomer and a methacrylic acid ester monomer (hereinafter, acrylic acid and methacrylic acid may be collectively referred to as "(meth)acrylic acid").

Specific examples of the (meth)acrylic acid ester monomer include an alkyl (meth)acrylic acid ester monomer and an aryl (meth)acrylic acid ester monomer.

The alkyl (meth)acrylic acid ester monomer and the aryl (meth)acrylic acid ester monomer can be each a monomer in which any hydrogen atom of an alkyl group or of an aryl group is substituted by, for example, a halogen atom, a hydroxyl group, an epoxy group, an amino group, a cyano group, or an alkoxy group.

Specific examples of the alkyl (meth)acrylic acid ester monomer include methyl (meth)acrylate, ethyl (meth)acrylate, butyl (meth)acrylate, 2-ethylhexyl (meth)acrylate, trifluoroethyl (meth)acrylate, tetrafluoropropyl (meth)acrylate, hydroxyethyl (meth)acrylate, hydroxypropyl (meth)acrylate, glycidyl (meth)acrylate, dimethylaminoethyl (meth)acrylate, cyanomethyl (meth)acrylate, 2-cyanoethyl (meth)acrylate, 1-cyanopropyl (meth)acrylate, 2-ethyl-6-cyanohexyl (meth)acrylate, 3-cyanopropyl (meth)acrylate, methoxymethyl (meth)acrylate, ethoxyethyl (meth)acrylate, methoxyethoxyethyl (meth)acrylate, and 2-methoxyethyl (meth)acrylate.

Specific examples of the α,β-ethylenically unsaturated polycarboxylic acid ester monomer include an α,β-ethylenically unsaturated dicarboxylic acid diester monomer and an α,β-ethylenically unsaturated tricarboxylic acid triester monomer.

Specific examples of the α,β-ethylenically unsaturated dicarboxylic acid diester monomer include: maleic acid diester monomers such as diethyl maleate and dibutyl maleate; fumaric acid diester monomers such as diethyl fumarate and dibutyl fumarate; and itaconic acid diester monomers such as dimethyl itaconate and diethyl itaconate.

Specific examples of the α,β-ethylenically unsaturated amide monomer include amide derivatives of (meth)acrylic acid. Typical examples of the amide derivatives include (meth)acrylamide, N-methylol (meth)acrylamide, N,N-dimethylol (meth)acrylamide, N-methoxymethyl (meth)acrylamide, and N-propoxymethyl (meth)acrylamide.

Specific examples of the alkyl vinyl ether monomer include methyl vinyl ether, ethyl vinyl ether, n-propyl vinyl ether, isopropyl vinyl ether, n-butyl vinyl ether, isobutyl vinyl ether, cyclohexyl vinyl ether, fluoroethyl vinyl ether, 2,2,2-trifluoroethyl vinyl ether, and 2,2,3,3,3-pentafluoropropyl vinyl ether.

The other monomer can be a crosslinkable monomer. Examples of the crosslinkable monomer include: polyvinyl aromatic monomers such as divinylbenzene; and polyacrylate monomers such as polyethyleneglycol di(meth)acrylate, polypropyleneglycol di(meth)acrylate, trimethylolpropane tri(meth)acrylate, and pentaerythritol (meth)acrylate.

The above examples of the other monomer can be used alone or in combination of two or more kinds.

A content of the other monomer is not limited to a particular content, and is preferably 19.5 wt % or less, more preferably 14 wt % or less, and still more preferably 9 wt % or less. The content of the other monomer of 19.5 wt % or less makes it possible to obtain a dip-molded article that is well-balanced in texture and tensile strength.

[Method of Producing Latex (A)]

A method of producing the latex (A) of the nitrile-group-containing highly saturated copolymer rubber (a), which latex (A) is contained in the dip-molding composition of the present invention, is not limited to a particular method, and is preferably a method including the steps of (i) subjecting a desired monomer to emulsion polymerization in the presence of water and an emulsifier so as to give latex, and (ii) hydrogenating at least part of a carbon-carbon double bond of a conjugated diene monomer unit in a copolymer contained in the latex.

The emulsifier for use in the emulsion polymerization can be typically an anionic surfactant, a cationic surfactant, a nonionic surfactant, an ampholytic surfactant, or the like. Meanwhile, a polymerization initiator and the like can be any of polymerization initiators and the like typically used in emulsion polymerization.

A polymerization method is also not limited to a particular method, and can be any one of a batch type method, a semibatch type method, and a continuous type method.

A polymerization temperature is not limited to a particular temperature, and is preferably 0° C. to 95° C., and more preferably 5° C. to 70° C.

For the polymerization, a polymerization auxiliary material typically usable in emulsion polymerization can also be used as appropriate. Examples of such an auxiliary material include a molecular weight modifier, a particle size modifier, a chelator, and an oxygen capture agent.

[Hydrogenation]

The latex (A) can be obtained by hydrogenating, in the presence of a hydrogenation catalyst, at least part of the carbon-carbon double bond of the conjugated diene monomer unit in the copolymer contained in the latex obtained by the emulsion polymerization.

Examples of the hydrogenation catalyst include water-soluble compounds of and water-dispersible compounds of platinum group elements such as ruthenium, rhodium, palladium, osmium, iridium, and platinum. The hydrogenation catalyst can be, for example, dissolved or dispersed in the latex rather than supported by a carrier, when provided for the hydrogenation reaction. More specifically, the hydrogenation catalyst is preferably a palladium compound or a rhodium compound, and particularly preferably a palladium compound. The platinum group element compounds can also be used in combination of two or more kinds. In such a case, it is still preferable to use a palladium compound as a main catalytic component.

The palladium compound is not limited to a particular one, and can be any palladium compound having hydrogenation catalytic activity. The palladium compound is preferably water-soluble or water-dispersible, and more preferably water-soluble. The palladium compound takes the form of, for example, a salt or a complex salt.

Examples of the palladium compound include: organic acid salts such as palladium acetate and palladium cyanide; halides such as palladium fluoride, palladium chloride, palladium bromide, and palladium iodide; oxygen acid salts such as palladium nitrate and palladium sulfate; palladium oxide; palladium hydroxide; palladium compounds such as dichloro(cyclooctadiene)palladium, dichloro(norbornadiene) palladium, dichlorobis(triphenylphosphine)palladium, sodium tetrachloropalladate, and ammonium hexachloropalladate; and complex salts such as potassium tetracyanopalladate.

Among the above examples, the palladium compound is preferably palladium acetate, palladium nitrate, palladium sulfate, palladium chloride, sodium tetrachloropalladate, and ammonium hexachloropalladate, and more preferably palladium acetate, palladium nitrate, and palladium chloride.

Examples of the rhodium compound include: halides such as rhodium chloride, rhodium bromide, and rhodium iodide; inorganic acid salts such as rhodium nitrate and rhodium sulfate; organic acid salts such as rhodium acetate, rhodium formate, rhodium propionate, rhodium butyrate, rhodium valerate, rhodium naphthenate, and rhodium acetylacetonate; rhodium oxide; and rhodium trihydroxide.

The platinum group element compound can be one available in the market or can be prepared by a conventional method.

A method of dissolving or dispersing the platinum group element compound in the latex is not limited to a particular method. Examples of the method include (i) a method in which the compound is directly added to the latex, and (ii) a method in which the compound is first dissolved or dispersed in water and is then added to the latex.

A hydrogenation temperature is preferably 0° C. to 200° C., more preferably 5° C. to 150° C., and still more preferably 10° C. to 100° C. The reaction temperature of 200° C. or lower allows for inhibition of side reactions such as hydrogenation of a nitrile group. The reaction temperature of 0° C. or higher makes it possible to obtain an adequate reaction speed.

A hydrogen pressure is preferably an atmospheric pressure to 20 MPa, more preferably the atmospheric pressure to 15 MPa, and still more preferably the atmospheric pressure to 10 MPa. A reaction time is not particularly limited, and is preferably 30 minutes to 50 hours.

Though the nitrile-group-containing highly saturated copolymer rubber (a) is in a latex form when the hydrogenation reaction is performed, the hydrogenation reaction proceeds rapidly if the hydrogenation reaction is performed under a basic condition. A hydrogenation ratio of the nitrile-group-containing highly saturated copolymer rubber (a) (i.e., a ratio of a hydrogenated carbon-carbon double bond relative to total carbon-carbon double bonds contained in a polymer prior to the hydrogenation reaction) can be arbitrarily controlled within a range of 1% to 100% by appropriately changing the above reaction conditions. The hydrogenation ratio that is expressed in an iodine value is, as described above, preferably 100 or less, and more preferably 50 or less.

The dip-molding composition of the present invention preferably further contains a crosslinking agent. The dip-molding composition further containing a crosslinking agent makes it possible to obtain a dip-molded article having more excellent tensile strength. The dip-molding composition more preferably further contains a crosslinking promoter so that a crosslinking reaction can proceed at an appropriate speed. The dip-molding composition can also contain zinc oxide if desired.

The latex (A) contained in the dip-molding composition of the present invention has excellent compatibility with a crosslinking agent, a crosslinking promotor, and zinc oxide, and thereby prevents formation of coarse and large agglomerations when mixed with the crosslinking agent, the crosslinking promotor, and zinc oxide. This makes it possible to obtain a dip-molded article having an even film thickness.

Specific examples of the crosslinking agent include: sulfurs such as powdered sulfur, sublimed sulfur, precipitated sulfur, colloidal sulfur, surface-treated sulfur, and insoluble sulfur; polyamines such as hexamethylene diamine, hexamethylene diamine carbamate, 2,2-bis[4-(4-aminophenoxy)phenyl]propane, triethylene tetramine, and tetraethylene pentamine; and an organic peroxide crosslinking agent. Among the above examples, sulfurs are preferable.

The organic peroxide crosslinking agent can be any conventionally-known one. Examples of the organic peroxide crosslinking agent include dicumyl peroxide, cumene hydroperoxide, t-butyl cumyl peroxide, p-menthane hydroperoxide, di-t-butylperoxide, 1,3-bis(t-butylperoxy isopropyl)benzene, 1,4-bis(t-butylperoxy isopropyl)benzene, 1,1-di-t-butylperoxy-3,3-trimethyl cyclohexane, 4,4-bis-(t-butylperoxy)-n-butylvalerate, 2,5-dimethyl-2,5-di-t-butylperoxy hexane, 2,5-dimethyl-2,5-di-t-butylperoxy hexyne-3, 1,1-di-t-butylperoxy-3,5,5-trimethyl cyclohexane, p-chlorobenzoyl peroxide, t-butylperoxy isopropyl carbonate, t-butylperoxy benzoate 1,1-bis(t-hexylperoxy)3,3,5-trimethyl cyclohexane, 1,1-bis(t-hexylperoxy) cyclohexane, 1,1-bis(t-butylperoxy)3,3,5-trimethyl cyclohexane, 1,1-bis(t-butylperoxy)cyclohexane, 1,1-bis(t-butylperoxy)cyclododecane, 2,2-bis(4,4-di-t-butylperoxy cyclohexyl)propane, α,α'-bis(t-butylperoxy-m-isopropyl)benzene, 2,5-dimethyl-2,5-bis(t-butylperoxy)hexane, di-t-butylperoxide diisobutyryl peroxide, di-2,4-dichlorobenzoyl peroxide, di-3,5,5-trimethyl hexanoyl peroxide, dioctanoyl peroxide, dilauroyl peroxide, distearoyl peroxide, disuccinic acid peroxide, di-m-toluoyl peroxide, dibenzoyl peroxide, di-n-propylperoxy dicarbonate, di-isopropylperoxy dicarbonate, bis-(4-t-butyl cyclohexyl) peroxy dicarbonate, di-2-ethoxyethylperoxy dicarbonate, di-2-ethylhexylperoxy dicarbonate, di-2-methoxybutylperoxy dicarbonate, di(3-methyl-3-methoxybutyl)peroxy dicarbonate, (α,α'-neodecanoylperoxy)di-isopropyl benzene, cumylperoxy neodecanoate, 1,1,3,3-tetramethyl-butylperoxy neodecanoate, 1-cyclohexyl-1-methylethylperoxy neodecanoate, 1-hexylperoxy neodecanoate, t-butylperoxy neodecanoate, t-hexylperoxy pivalate, t-butylperoxy pivalate, 1,1,3,3-tetramethylbutylperoxy-2-ethylhexanoate, 2,5-dimethyl-2,5-bis(2-ethylhexanoylperoxy) hexane, 1-cyclohexyl-1-methylethylperoxy-2-ethylhexanoate, t-butylperoxy-2-ethylhexanoate, t-butylperoxy isobutyrate, t-hexylperoxy isopropyl monocarbonate, t-butylperoxy maleic acid, t-butylperoxy-3,5,5-trimethylhexanoate, t-butylperoxy laurate, 2,5-dimethyl-2,5-bis(m-toluoylperoxy)hexane, t-butylperoxy isopropyl monocarbonate, t-butylperoxy-2-ethylhexyl monocarbonate, 1-hexylperoxy benzoate, 2,5-dimethyl-2,5-bis(benzoylperoxy)hexane, t-butylperoxy acetate, t-butylperoxy benzoate, bis-t-butylperoxy isophthalate, (α,α'-neodecanoylperoxy)di-isopropyl benzene, cumylperoxy neodecanoate, 1,1,3,3-tetramethylbutylperoxy neodecanoate, 1-cyclohexyl-1-methylethylperoxy neodecanoate, 1-hexylperoxy neodecanoate, t-butylperoxy neodecanoate, t-hexylperoxy pivalate, t-butylperoxy pivalate, 1,1,3,3-tetramethylbutylperoxy-2-ethylhexanoate, 2,5-dimethyl-2,5,-bis(2-ethylhexanoylperoxy) hexane, 1-cyclohexyl-1-methylethylperoxy-2-ethylhexanoate, t-butylperoxy-2-ethylhexanoate, t-butylperoxy isobutyrate, t-hexylperoxy isopropyl monocarbonate, t-butylperoxy maleic acid, t-butylperoxy-3,5,5-trimethylhexanoate, t-butylperoxy laurate, 2,5-dimethyl-2,5-bis(m-toluoylperoxy)hexane, t-butylperoxy isopropyl monocarbonate, t-butylperoxy-2-ethylhexyl monocarbonate, 1-hexylperoxy benzoate, 2,5-dimethyl-2,5-bis(benzoylperoxy)hexane, t-butylperoxy acetate, t-butylperoxy benzoate, and bis-t-butylperoxy isophthalate. Among the above examples, 1,3-bis(t-butylperoxy isopropyl)benzene is preferable. Note that the above organic peroxide crosslinking agents can be used alone or in combination of two or more kinds.

An amount of the crosslinking agent used is preferably 0.1 parts by weight to 5 parts by weight, more preferably 0.3 parts by weight to 3 parts by weight, and particularly preferably 0.5 parts by weight to 2 parts by weight, relative to 100 parts by weight of a solid content of the latex (A).

Examples of the crosslinking promotor include: dithiocarbamic acids such as diethyl dithiocarbamic acid, dibutyl dithiocarbamic acid, di-2-ethylhexyl dithiocarbamic acid, dicyclohexyl dithiocarbamic acid, diphenyl dithiocarbamic acid, and dibenzyl dithiocarbamic acid, and zinc salts of such dithiocarbamic acids; basic crosslinking promotors each having a cyclic amidine structure, such as 2-mercapto benzothiazole, zinc 2-mercapto benzothiazole, 2-mercaptothiazoline, dibenzothiazyl.disulfide, 2-(2,4-dinitrophenylthio)benzothiazole, 2-(N,N-diethylthio.carbamoyl)benzothiazole, 2-(2,6-dimethyl-4-morpholinothio)benzothiazole, 2-(4'-morpholino.dithio)benzothiazole, 4-morpholinyl-2-benzothiazyl.disulfide, 1,3-bis(2-benzothiazyl.mercaptomethyl)urea, 1,8-diazabicyclo[5,4,0]undecene-7 (which hereinafter may be abbreviated as "DBU"), 1,5-diazabicyclo[4,3,0]nonene-5 (which hereinafter may be, abbreviated as "DBN"), 1-methylimidazole, 1-ethylimidazole, 1-phenylimidazole, 1-benzylimidazole, 1,2-dimethylimidazole, 1-ethyl-2-methylimidazole, 1-methoxyethylimidazole, 1-phenyl-2-methylimidazole, 1-benzyl-2-methylimidazole, 1-methyl-2-phenylimidazole, 1-methyl-2-benzylimidazole, 1,4-dimethylimidazole, 1,5-dimethylimidazole, trimethylimidazole, 1,4-dimethyl-2-ethylimidazole, 1-methyl-2-methoxyimidazole, 1-methyl-2-ethoxyimidazole, 1-methyl-4-methoxyimidazole, 1-methyl-2-methoxyimidazole, 1-ethoxymethyl-2-methylimidazole, 1-methyl-4-nitroimidazole, 1,2-dimethyl-5-nitroimidazole, 1,2-dimethyl-5-aminoimidazole, 1-methyl-4-(2-aminoethyl)imidazole, 1-methylbenzimidazole, 1-methyl-2-benzylbenzimidazole, 1-methyl-5-nitrobenzimidazole, 1-methylimidazoline, 1,2-dimethylimidazoline, 1,2,4-trimethylimidazoline, 1,4-dimethyl-2-ethylimidazoline, 1-methyl-phenylimidazoline, 1-methyl-2-benzylimidazoline, 1-methyl-2-ethoxyimidazoline, 1-methyl-2-heptylimidazoline, 1-methyl-2-undecylimidazoline, 1-methyl-2-heptadecylimidazoline, 1-methyl-2-ethoxymethylimidazoline, and 1-ethoxymethyl-2-methylimidazoline; guanidine-based basic crosslinking promotors such as tetramethylguanidine, tetraethylguanidine, diphenylguanidine, 1,3-di-ortho-tolylguanidine, and orthotolylbiguanide; and aldehydeamine-based basic crosslinking promotors such as n-butyraldehyde aniline and acetaldehyde ammonia. Among the above examples, zinc diethyl dithiocarbamate, zinc dibuthyl dithiocarbamate, 2-mercaptobenzothiazole, and zinc 2-mercaptobenzothiazole are preferable. These crosslinking promotors can be used alone or in combination of two or more kinds.

An amount of the crosslinking promotor used is preferably 0.1 parts by weight to 20 parts by weight, more preferably 0.5 parts by weight to 10 parts by weight, and particularly preferably 1 part by weight to 5 parts by weight, relative to 100 parts by weight of the solid content of the latex (A).

An amount of zinc oxide used is preferably 10 parts by weight or less, more preferably 8 parts by weight or less, and particularly preferably 0.5 parts by weight to 5 parts by weight, relative to 100 parts by weight of the solid content of the latex (A).

In a case where the nitrile-group-containing highly saturated copolymer rubber (a) of the latex (A) contains the α,β-ethylenically unsaturated acid monomer unit, an acid radical and zinc oxide in the monomer unit react with each other and form an ionic bond. In such a case, the zinc oxide serves as a crosslinking agent.

The dip-molding composition of the present invention can further contain, if desired, additives such as a pH adjustor, a thickener, an anti-aging agent, a dispersant, a colorant, a filler, a softener, and an antiseptic agent.

Examples of the colorant include white pigments such as titanium oxide ($TiO_2$).

The latex (A) can be used in combination with other latex such as natural rubber latex, isoprene rubber latex, and nitrile rubber latex, as long as such other latex does not hamper attainment of the object of the present invention.

When the latex (A) is mixed with, for example, a crosslinking agent, a crosslinking promotor, zinc oxide, an additive, and other latex as described above in the dip-molding composition, the dip-molding composition has a solid content concentration of preferably 20 wt % to 45 wt %, more preferably 20 wt % to 40 wt %, and still more preferably 25 wt % to 40 wt %. Further, the dip-molding composition has a pH of preferably 8.5 to 12, and more preferably 9 to 11.

<Dip-Molded Article>

The dip-molded article of the present invention is produced by dip molding of the dip-molding composition of the present invention.

A method of the dip molding can be any conventionally known method. Examples of the method of the dip molding include a straight dipping process, an anode coagulant dipping process, and a Teague coagulant dipping process. Among these methods, the anode coagulant dipping process is preferable since it makes it possible to obtain a dip-molded article having an even thickness.

In a case where the anode coagulant dipping process is employed, for example, a mold for dip molding is first dipped into a solution of a coagulant, so that the coagulant adheres to a surface of the mold. The mold is then dipped into the dip-molding composition, so that a dip molded layer is formed on the surface of the mold.

Examples of the coagulant include: metal halides such as barium chloride, calcium chloride, magnesium chloride, zinc chloride, and aluminum chloride; nitrates such as barium nitrate, calcium nitrate, and zinc nitrate; acetates such as barium acetate, calcium acetate, and zinc acetate; and sulfates such as calcium sulfate, magnesium sulfate, and aluminum sulfate. Among the above examples, calcium chloride and calcium nitrate are preferable.

The coagulant is mixed with, for example, water, alcohol, or a mixture of water and alcohol, and used in the form of a solution. A concentration of the coagulant is preferably 5 wt % to 50 wt %, and more preferably 10 wt % to 30 wt %.

A resultant dip molded layer can be crosslinked by heat treatment. In such a case, for example, the resultant dip molded layer can be immersed in water (preferably, warm water at 30° C. to 70° C.) for 1 minute to 60 minutes so that water-soluble impurities (e.g., excess emulsifier and coagulant) can be removed prior to the heat treatment. Note that this process can be alternatively performed after the heat treatment of the dip molded layer. The process, however, is preferably performed prior to the heat treatment because the water-soluble impurities can be more efficiently removed.

The resultant dip molded layer is then crosslinked by heat treatment at a temperature of 100° C. to 150° C. for 10 minutes to 120 minutes. A method of heating can be external heating by infrared rays or hot air, or internal heating by radio-frequency waves. Among these heating methods, heating by hot air is preferable.

The dip-molded article is then obtained by removing the dip molded layer thus crosslinked from the mold for dip molding. The layer can be removed by stripping the dip-molded article off the mold, for example, manually or by water pressure or compressed air pressure.

After this removal, the dip-molded article can be heat-treated at a temperature of 60° C. to 120° C. for 10 minutes to 120 minutes.

The dip-molded article can be further provided with a surface-treated layer on an internal surface and/or an external surface of the dip-molded article.

It is possible to easily obtain, as the dip-molded article of the present invention, a dip-molded article having a tensile strength of 35 MPa or more, preferably 40 MPa or more, and still more preferably 45 MPa. In such a dip-molded article having a tensile strength of 35 MPa or more, the tensile strength can be suitably improved by hydrogenation for causing the nitrile-group-containing highly saturated copolymer rubber (a) of the latex (A) to have a lower iodine value and/or by increasing the content of the α,β-ethylenically unsaturated acid monomer unit.

The dip-molded article of the present invention has excellent post-heat-aging cold resistance. The dip-molded article therefore can be suitably used in a cold environment even after having been placed in a hot environment. That is, even in a case where (i) a strip having a width of 4 cm and a length of 10 cm is taken from the dip-molded article of the present invention and (ii) the strip is placed in an environment at a temperature of 130° C. for 6 days and then bent in an environment at a temperature of −30° C. such that tangents at respective lengthwise ends of the strip curved in a length direction of the strip an angle of 90°, no crack occurs in the strip. The dip-molded article is therefore usable as a dip-molded article that is to have thermal history including a great variation range of temperature to which the dip-molded article is to be exposed on a transportation route. Such a dip-molded article excellent in post-heat-aging cold resistance can be obtained by hydrogenation for causing the nitrile-group-containing highly saturated copolymer rubber (a) to have a lower iodine value and/or by adjustment of the content of the α,β-ethylenically unsaturated nitrile monomer unit.

The dip-molded article of the present invention can be configured to have a thickness of approximately 0.03 mm to approximately 3 mm, and is thus particularly suitable for a thin article having a thickness of 0.05 mm to 1 mm. Specifically, the dip-molded article is applicable to: medical products such as nipples for baby bottles, droppers, conduits, and water pillows; toys and sports goods such as balloons, dolls, and balls; industrial goods such as bags for pressure bag molding and bags for gas storage; gloves for surgical, housework, agricultural, fishing, and industrial uses; and fingertips. Among the above applications, the dip-molded article is particularly suitably applied to thin surgical gloves.

The present invention is not limited to the foregoing embodiments, but can be variously altered by a skilled person in the art within the scope of the claims. An embodiment derived from a proper combination of technical means each disclosed in the foregoing embodiments is also encompassed in the technical scope of the present invention.

EXAMPLES

The following description will more specifically discuss the present invention with reference to Examples and Comparative Examples. Note that the present invention is not limited to Examples. Parts and percentages used in Examples and Comparative Examples indicate parts by weight and percentages by weight, respectively, unless otherwise noted. Tests and evaluations were performed in the following manner.

[Iodine Value]

After 100 grams of latex was solidified with 1 liter of methanol, the latex was dried in vacuum at 60° C. overnight. Then, an iodine value of a dried rubber was measured in accordance with JIS K6235.

[Tensile Test of Dip-Molded Article (Vulcanized Film)]

(Preparation of Specimen for Evaluation of Physical Properties of Dip-Molded Article)

In accordance with ASTM D412, a dip-molded article in the form of a rubber glove was punched by a dumbbell-shaped cutting die (Die C), so that a specimen was obtained.

(Measurement of Tensile Strength, Tensile Stress, and Elongation)

With use of the specimen obtained as above, tensile strength, 100% tensile stress, 200% tensile stress, 300% tensile stress, and elongation of the dip-molded article were measured in accordance with JIS K6251.

[Cold Bend Test after Heat Aging]

A strip as a specimen was cut out from the dip-molded article so as to have a width of 2 cm and a length of 10 cm. This specimen was heat-treated in a Geer oven at 130° C. for 6 days. The specimen was then bent by 90 degrees in a cryostat at −30° C. Then, an appearance of the specimen was visually observed. A specimen having a crack was evaluated as "poor", whereas a specimen having no crack was evaluated as "good".

Synthesis Example 1 (Preparation of Nitrile-Group-Containing Highly Saturated Copolymer Rubber Latex (A1))

Into a reaction container, 180 parts of ion-exchange water, 25 parts of a 10 wt % solution of sodium dodecylbenzene sulfonate, 35 parts of acrylonitrile, 4 parts of methacrylic acid, and 0.5 parts of t-dodecylmercaptan (molecular weight modifier) were introduced in this order. The reaction container was purged with nitrogen 3 times, and 61 parts of 1,3-butadiene was introduced into the reaction container. While the reaction container was kept at 5° C., 0.1 parts of cumene hydroperoxide (polymerization initiator) was introduced into the reaction container to initiate a polymerization reaction. While a mixture thus obtained was being stirred, the polymerization reaction was continued until a polymerization conversion rate reached 90%. When the polymerization conversion rate reached 90%, 0.1 parts of a 10 wt % solution of hydroquinone (polymerization terminator) was added to terminate the polymerization reaction. Residual monomers were then removed at a water temperature of 60° C., so that a nitrile-group-containing copolymer rubber latex (x) (solid content concentration: approximately 30 wt %) was obtained.

Part of the nitrile-group-containing copolymer rubber latex (x) was taken as a sample. This sample was solidified with methanol, washed with water, and dried, so that a nitrile-group-containing copolymer rubber was obtained. A unit amount of each monomer contained in the nitrile-group-containing copolymer rubber was determined by $^1$H-NMR and $^{13}$C-NMR. Table 2 shows determination results.

Next, the nitrile-group-containing copolymer rubber latex (x) and a palladium catalyst (a solution obtained by mixing a 1 wt % acetone solution of palladium acetate and ion-exchange water which was equal in weight to the 1 wt % acetone solution) were added into an autoclave so that a palladium content would be 1000 ppm by weight, relative to a dry weight of rubber contained in the nitrile-group-containing copolymer rubber latex (x). Thereafter, a hydrogenation reaction was performed under hydrogen pressure of 3 MPa at a temperature of 50° C. for 6 hours, so that a solid content concentration was adjusted. As a result, a nitrile-group-containing highly saturated copolymer rubber latex (A1) (solid content concentration: 40 wt %) was prepared.

A Part of the latex (A1) was taken as a sample. The sample was solidified with methanol, washed with water, and dried, so that a nitrile-group-containing highly saturated copolymer rubber was obtained. A unit amount of each monomer contained in the nitrile-group-containing highly saturated copolymer rubber was determined by $^1$H-NMR and $^{13}$C-NMR, and an iodine value of the nitrile-group-containing highly saturated copolymer rubber was determined as described above. Table 2 shows determination results.

Synthesis Example 2 (Preparation of Nitrile-Group-Containing Highly Saturated Copolymer Rubber Latex (A2))

A nitrile-group-containing highly saturated copolymer rubber latex (A2) (solid content concentration: 40 wt %) was prepared as in Synthesis Example 1, except that the palladium catalyst was added such that a palladium content would be 1200 ppm by weight, relative to a dry weight of rubber contained in the nitrile-group-containing copolymer rubber latex (x). Thereafter, a unit amount of each monomer contained in a nitrile-group-containing highly saturated copolymer rubber contained in the nitrile-group-containing highly saturated copolymer rubber latex (A2) and an iodine value of the nitrile-group-containing highly saturated copolymer rubber were determined as in Synthesis Example 1. Table 2 shows determination results.

Synthesis Example 3 (Preparation of Nitrile-Group-Containing Highly Saturated Copolymer Rubber Latex (A3))

A nitrile-group-containing highly saturated copolymer rubber latex (A3) (solid content concentration: 40 wt %) was prepared as in Synthesis Example 1, except that the palladium catalyst was added such that a palladium content would be 900 ppm by weight, relative to a dry weight of rubber contained in the nitrile-group-containing copolymer rubber latex (x). Thereafter, a unit amount of each monomer contained in a nitrile-group-containing highly saturated copolymer rubber contained in the nitrile-group-containing highly saturated copolymer rubber latex (A3) and an iodine value of the nitrile-group-containing highly saturated copolymer rubber were determined as in Synthesis Example 1. Table 2 shows determination results.

Synthesis Example 4 (Preparation of Nitrile-Group-Containing Highly Saturated Copolymer Rubber Latex (A4))

A nitrile-group-containing highly saturated copolymer rubber latex (A4) (solid content concentration: 39 wt %) was prepared as in Synthesis Example 1, except that an amount of acrylonitrile was changed from 35 parts to 33.5 parts and an amount of methacrylic acid was changed from 4 parts to 5.5 parts. Thereafter, a unit amount of each monomer contained in a nitrile-group-containing highly saturated copolymer rubber contained in the nitrile-group-containing highly saturated copolymer rubber latex (A4) and an iodine value of the nitrile-group-containing highly saturated copolymer rubber were determined as in Synthesis Example 1. Table 2 shows determination results.

Synthesis Example 5 (Preparation of Nitrile-Group-Containing Copolymer Rubber Latex (B1))

Into a reaction container, 150 parts of ion-exchange water, 1.5 parts of sodium dodecylbenzene sulfonate, 0.2 parts of potassium persulfate, 0.1 parts of sodium ethylenediamine tetraacetate, 27.0 parts of acrylonitrile, 67.5 parts of 1,3-butadiene, 5.5 parts of methacrylic acid, and 0.5 parts of t-dodecyl mercaptan were introduced. Then, a polymerization reaction was initiated by increasing a temperature within a polymerization system to 35° C.

When a polymerization conversion rate reached 50%, 1.0 parts of a 10% solution of sodium dodecylbenzene sulfonate was added at one time as an additional emulsifier.

The polymerization reaction was continued until the polymerization conversion rate of all monomers reached 97%. When the polymerization conversion rate reached 97%, 0.1 parts of diethyl hydroxylamine was added to terminate the polymerization reaction. Unreacted monomers were distilled away from resultant latex, and a solid content concentration and a pH were adjusted. As a result, a nitrile-group-containing copolymer rubber latex (B1) (solid content concentration: approximately 40%) having a pH of 8.3 was obtained. Then, a unit amount of each monomer contained in a nitrile-group-containing copolymer rubber contained in the latex (B1) was determined as in Synthesis Example 1. Table 2 shows determination results.

Synthesis Example 6 (Preparation of Nitrile-Group-Containing Copolymer Rubber Latex (B2))

A nitrile-group-containing copolymer rubber latex (B2) (solid content concentration: approximately 40%, latex pH: 8.3) was prepared as in Synthesis Example 4, except that an amount of t-dodecyl mercaptan was changed to 1.0 part. A unit amount of each monomer contained in a nitrile-group-containing copolymer rubber contained in the latex (B2) was determined as in Synthesis Example 1. Table 2 shows determination results.

Example 1

First, a dispersion liquid of a crosslinking agent was prepared by mixing 1 part of sulfur, 1.5 parts of zinc oxide, 0.5 parts of zinc diethyl dithiocarbamate, 1.5 parts of titanium oxide, 0.03 parts of potassium hydroxide, and 5.63 parts of water. Then, 8.66 parts of this dispersion liquid of the crosslinking agent was added to 250 parts (corresponding to 100 parts of a solid content) of the nitrile-group-containing highly saturated copolymer rubber latex (A1) obtained in Synthesis Example 1. Thereafter, an appropriate amount of a 5% solution of potassium hydroxide and deionized water were added to a mixture of the dispersion liquid of the crosslinking agent and the latex (A1). As a result, a dip-molding composition (A'1) having a solid content concentration of 30% and a pH of 9.8 was obtained.

Further, a coagulant solution was prepared by mixing 20 parts of calcium nitrate, 0.05 parts of polyoxyethylene octylphenyl ether (nonionic emulsifier), and 80 parts of water. Then, a glove mold was dipped into the coagulant solution for 1 minute, taken out from the coagulant solution, and dried at 50° C. for 3 minutes, so that the coagulant adhered to the glove mold.

Subsequently, the glove mold to which the coagulant had adhered was dipped into the dip-molding composition (A'1) for 6 minutes, and taken out from the dip-molding composition (A'1). The glove mold on which a dip molded layer had been formed was dried at 25° C. for 3 minutes. The glove mold was then immersed into warm water at 40° C. for 3 minutes, so that water-soluble impurities were eluted.

Next, the glove mold was dried at 80° C. for 20 minutes and heat-treated at 120° C. for 25 minutes, so that the dip molded layer was crosslinked. At the end, the dip molded layer thus crosslinked was stripped off the glove mold. As a result, a dip-molded article (AA'1) in the shape of a glove was obtained. Thereafter, tensile strength, tensile stress, elongation of the dip-molded article (AA'1) were measured by the above-described methods. Table 1 shows measurement results.

Example 2

A dip-molded article (AA'2) was prepared as in Example 1, except that the nitrile-group-containing highly saturated copolymer rubber latex (A2) obtained in Synthesis Example 2 was used instead of the nitrile-group-containing highly saturated copolymer rubber latex (A1). The dip-molded article (AA'2) was evaluated as in Example 1. Table 1 shows evaluation results.

Example 3

A dip-molded article (AA'3) was prepared as in Example 1, except that the nitrile-group-containing highly saturated copolymer rubber latex (A3) obtained in Synthesis Example 3 was used instead of the nitrile-group-containing highly saturated copolymer rubber latex (A1). The dip-molded article (AA'3) was evaluated as in Example 1. Table 1 shows evaluation results.

Example 4

A dip-molded article (AA'4) was prepared as in Example 1, except that the nitrile-group-containing highly saturated copolymer rubber latex (A4) obtained in Synthesis Example 4 was used instead of the nitrile-group-containing highly saturated copolymer rubber latex (A1). The dip-molded article (AA'4) was evaluated as in Example 1. Table 1 shows evaluation results.

Comparative Example 1

A dip-molded article (BB'1) was prepared as in Example 1, except that the nitrile-group-containing copolymer rubber latex (B1) obtained in Synthesis Example 5 was used instead of the nitrile-group-containing highly saturated copolymer rubber latex (A1). The dip-molded article (BB'1) was evaluated as in Example 1. Table shows evaluation results.

Comparative Example 2

A dip-molded article (BB'2) was prepared as in Example 1, except that the nitrile-group-containing copolymer rubber latex (B2) obtained in Synthesis Example 6 was used instead of the nitrile-group-containing highly saturated copolymer rubber latex (A1). The dip-molded article (BB'2) was evaluated as in Example 1. Table 1 shows evaluation results.

Comparative Example 3

A dip-molded article (aa'1) was prepared as in Example 1, except that 333 parts of the nitrile-group-containing copolymer rubber latex (x) obtained in Synthesis Example 1 was used instead of 250 parts of the nitrile-group-containing highly saturated copolymer rubber latex (A1). The dip-molded article (aa'1) was evaluated as in Example 1. Table 1 shows evaluation results.

TABLE 1

|  | Example 1 | Example 2 | Example 3 | Example 4 | Comparative Example 1 | Comparative Example 2 | Comparative Example 3 |
|---|---|---|---|---|---|---|---|
| Latex | (A1) | (A2) | (A3) | (A4) | (B1) | (B2) | (x) |
| Iodine value | 32 | 22 | 49 | 30 | — | — | — |
| Tensile test of crosslinked films |  |  |  |  |  |  |  |
| Elongation (%) | 350 | 420 | 430 | 340 | 540 | 590 | 530 |
| Tensile strength (MPa) | 49.5 | 52.1 | 48.2 | 49.0 | 29.8 | 31.7 | 30.2 |

TABLE 1-continued

|  | Example 1 | Example 2 | Example 3 | Example 4 | Comparative Example 1 | Comparative Example 2 | Comparative Example 3 |
|---|---|---|---|---|---|---|---|
| 100% tensile stress (MPa) | 2.9 | 2.4 | 2.6 | 2.6 | 2.7 | 2.4 | 2.8 |
| 200% tensile stress (MPa) | 6.0 | 4.8 | 5.0 | 5.9 | 3.8 | 3.6 | 3.7 |
| 300% tensile stress (MPa) | 18.8 | 16.1 | 15.9 | 18.0 | 5.8 | 5.3 | 5.5 |
| Cold bend test after heat-aging |  |  |  |  |  |  |  |
| Crack | Good | Good | Good | Good | Poor | Poor | Poor |

TABLE 2

| Latex | Acrylonitrile unit (wt %) | 1,3-butadiene unit (wt %) (inclusive of hydrogenated part) | Methacrylic acid unit (wt %) | Iodine value |
|---|---|---|---|---|
| Nitrile-group-containing highly saturated copolymer rubber latex (A1) | 34.3 | 62.5 | 3.2 | 32 |
| Nitrile-group-containing highly saturated copolymer rubber latex (A2) | 34.3 | 62.5 | 3.2 | 22 |
| Nitrile-group-containing highly saturated copolymer rubber latex (A3) | 35.2 | 61.1 | 3.7 | 49 |
| Nitrile-group-containing highly saturated copolymer rubber latex (A4) | 33.9 | 62 | 5.1 | 30 |
| Nitrile-group-containing copolymer rubber latex (B1) | 27.2 | 67.5 | 5.3 | 319 |
| Nitrile-group-containing copolymer rubber latex (B2) | 27.1 | 67.5 | 5.3 | 317 |
| Nitrile-group-containing copolymer rubber latex (x) | 34.5 | 62 | 3.5 | 293 |

The following is clear from Table 1.

The dip-molded articles produced by dip-molding of the dip-molding compositions each containing the nitrile-group-containing highly saturated copolymer rubber latex specified by the present invention were excellent in tensile strength and post-heat-aging cold resistance (Examples 1 through 4).

In contrast, the dip-molded articles produced by dip-molding of the dip-molding compositions each containing the conventional nitrile-group-containing copolymer rubber latex were poor in tensile strength and post-heat-aging cold resistance (Comparative Examples 1 through 3).

INDUSTRIAL APPLICABILITY

The present invention is applicable to various dip-molded articles.

The invention claimed is:

1. A dip-molded article produced by dip-molding in a dip-molding composition, the composition comprising:
   a latex (A) containing a nitrile-group-containing highly saturated copolymer rubber (a), wherein:
   the nitrile-group-containing highly saturated copolymer rubber (a) contains: (i) an α,β-ethylenically unsaturated nitrile monomer unit, (ii) an α,β-ethylenically unsaturated acid monomer unit in an amount of from 2 wt % to 6 wt %, and (iii) a conjugated diene monomer unit, and
   the nitrile-group-containing highly saturated copolymer rubber (a) is obtained by hydrogenating at least part of the conjugated diene monomer unit, and
   wherein no crack occurs in a strip of the dip-molded article in a case where (i) the strip is cut from the dip-molded article so as to have a width of 2 cm and a length of 10 cm, and (ii) the strip is placed in an environment at a temperature of 130° C. for 6 days and then bent in an environment at a temperature of −30° C. such that tangents at respective lengthwise ends of the strip curved in a length direction of the strip make an angle of 90°.

2. The dip-molding article as set forth in claim 1, wherein: the nitrile-group-containing highly saturated copolymer rubber (a) has an iodine value of 100 or less.

3. The dip-molding article as set forth in claim 1, wherein the composition further comprises a crosslinking agent.

4. The dip-molded article as set forth in claim 1, wherein the dip-molded article is a glove.

5. The dip-molded article as set forth in claim 1, wherein the dip-molded article has a tensile strength of 35 MPa or more.

6. The dip-molded article as set forth in claim 3, wherein the crosslinking agent is zinc oxide.

* * * * *